US009901262B2

(12) United States Patent
Hammerling (10) Patent No.: US 9,901,262 B2
(45) Date of Patent: Feb. 27, 2018

(54) MOBILE TRANSDUCER HOLDER ASSEMBLY

(71) Applicant: ProMedica Health System, Inc., Toledo, OH (US)

(72) Inventor: Lee Hammerling, Toledo, OH (US)

(73) Assignee: PROMEDICA HEALTH SYSTEM, INC., Toledo, OH (US)

( * ) Notice: Subject to any disclaimer, the term of this patent is extended or adjusted under 35 U.S.C. 154(b) by 561 days.

(21) Appl. No.: 14/575,108

(22) Filed: Dec. 18, 2014

(65) Prior Publication Data

US 2015/0173681 A1 Jun. 25, 2015

Related U.S. Application Data

(60) Provisional application No. 61/917,488, filed on Dec. 18, 2013.

(51) Int. Cl.
*A61B 5/04* (2006.01)
*A61B 5/021* (2006.01)
*A61B 5/0215* (2006.01)
*A61B 5/03* (2006.01)
*A61B 5/0408* (2006.01)
*A61B 5/0416* (2006.01)

(52) U.S. Cl.
CPC ........ *A61B 5/02141* (2013.01); *A61B 5/0215* (2013.01); *A61B 5/031* (2013.01); *A61B 5/0416* (2013.01); *A61B 5/04087* (2013.01)

(58) Field of Classification Search
CPC ... A61B 5/02141; A61B 5/0215; A61B 5/031; A61B 5/04087; A61B 5/0416
See application file for complete search history.

(56) References Cited

U.S. PATENT DOCUMENTS

| | | | |
|---|---|---|---|
| 4,576,181 A | 3/1986 | Wallace et al. | |
| 4,974,593 A | 12/1990 | Ng | |
| 5,094,243 A | 3/1992 | Puy et al. | |
| 6,048,323 A | 4/2000 | Hon | |
| 6,378,828 B1 | 4/2002 | Valiulis et al. | |
| 6,928,948 B1 | 8/2005 | Shannon | |
| 7,857,763 B2 | 12/2010 | Tai | |
| 2005/0197585 A1* | 9/2005 | Brockway | A61B 5/411 600/486 |
| 2008/0306388 A1 | 12/2008 | Tanis et al. | |
| 2012/0109019 A1 | 5/2012 | Schneider et al. | |
| 2012/0187261 A1 | 7/2012 | Cicero | |
| 2013/0121115 A1 | 5/2013 | Johnson | |

FOREIGN PATENT DOCUMENTS

WO 9002512 A1 3/1990

* cited by examiner

*Primary Examiner* — George Manuel
(74) *Attorney, Agent, or Firm* — Michael E. Dockins; Shumaker, Loop & Kendrick, LLP (57) ABSTRACT

A transducer holder assembly for attachment to a patient includes a support member with a contact surface and an oppositely disposed connection surface. The support member includes at least one electrode disposed on the contact surface. A first mating member is coupled to the connection surface. A housing is configured to receive and hold at least a portion of a transducer. The housing includes a second mating member configured to releasably mate with the first mating member via a snap-fit mechanism.

19 Claims, 9 Drawing Sheets

Fig. 8B

MOBILE TRANSDUCER HOLDER ASSEMBLY

RELATED APPLICATION

This application claims the benefit of U.S. Provisional Patent Application Ser. No. 61/917,488, filed Dec. 18, 2013, the entirety of which is hereby incorporated by reference for all purposes.

TECHNICAL FIELD

The present disclosure relates generally to a transducer holder and, more particularly, to a mobile transducer holder assembly for use with pressure monitoring and other technologies.

BACKGROUND

Transducers are used to monitor vital patient signs, such as blood pressure. Transducers must be in-line with the patient's heart to provide an accurate blood pressure reading. To ensure proper alignment, transducers are typically attached to a piece of medical equipment, such as an IV pole, and then adjusted to a height level with the patient's heart. When the patient is moved, however, the position of the transducer, and thus the IV pole, must be adjusted to maintain alignment with the patient's heart. Also during movement, numerous cords associated with the transducer can be difficult to manage without risk of accidently displacing the transducer.

SUMMARY

The present disclosure is generally directed to a transducer holder and, more particularly, to a mobile transducer holder assembly for use with pressure monitoring and other technologies.

In one aspect of the present disclosure, a transducer holder assembly for attachment to a patient includes a support member with a contact surface and an oppositely disposed connection surface. At least one electrode is disposed on the contact surface. A first mating member is coupled to the connection surface. A housing is configured to receive and hold at least a portion of a transducer. The housing includes a second mating member configured to releasably mate with the first mating member via a snap-fit mechanism.

In another aspect of the present disclosure, a transducer holder assembly for attachment to a patient includes a support member with a contact surface and an oppositely disposed connection surface. At least one electrode is disposed on the contact surface. A first mating member is coupled to the connection surface. A first housing is configured to receive and hold at least a portion of a transducer. A second housing is connected to a portion of the first housing. The second housing is configured to receive and hold at least a portion of a line-clearing mechanism. At least one of the first housing and the second housing includes a second mating member configured to releasably mate with the first mating member via a snap-fit mechanism.

In another aspect of the present disclosure, a method can include the step of providing a transducer holder assembly. The pressure transducer assembly can include a support member, at least one electrode, a first mating member and a housing. The support member can have a contact surface and an oppositely disposed connection surface. The at least one electrode can be disposed on the contact surface. The first mating member can be coupled to the connection surface. The housing can be configured to receive and hold at least a portion of the transducer. The housing can include a second mating member configured to releasably mate with the first mating member via a snap-fit mechanism.

BRIEF DESCRIPTION OF THE DRAWINGS

The foregoing and other features and advantages of the present disclosure will become apparent to one skilled in the art upon consideration of the following description of the disclosure and the accompanying drawings, in which.

DETAILED DESCRIPTION

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Figure 1A:
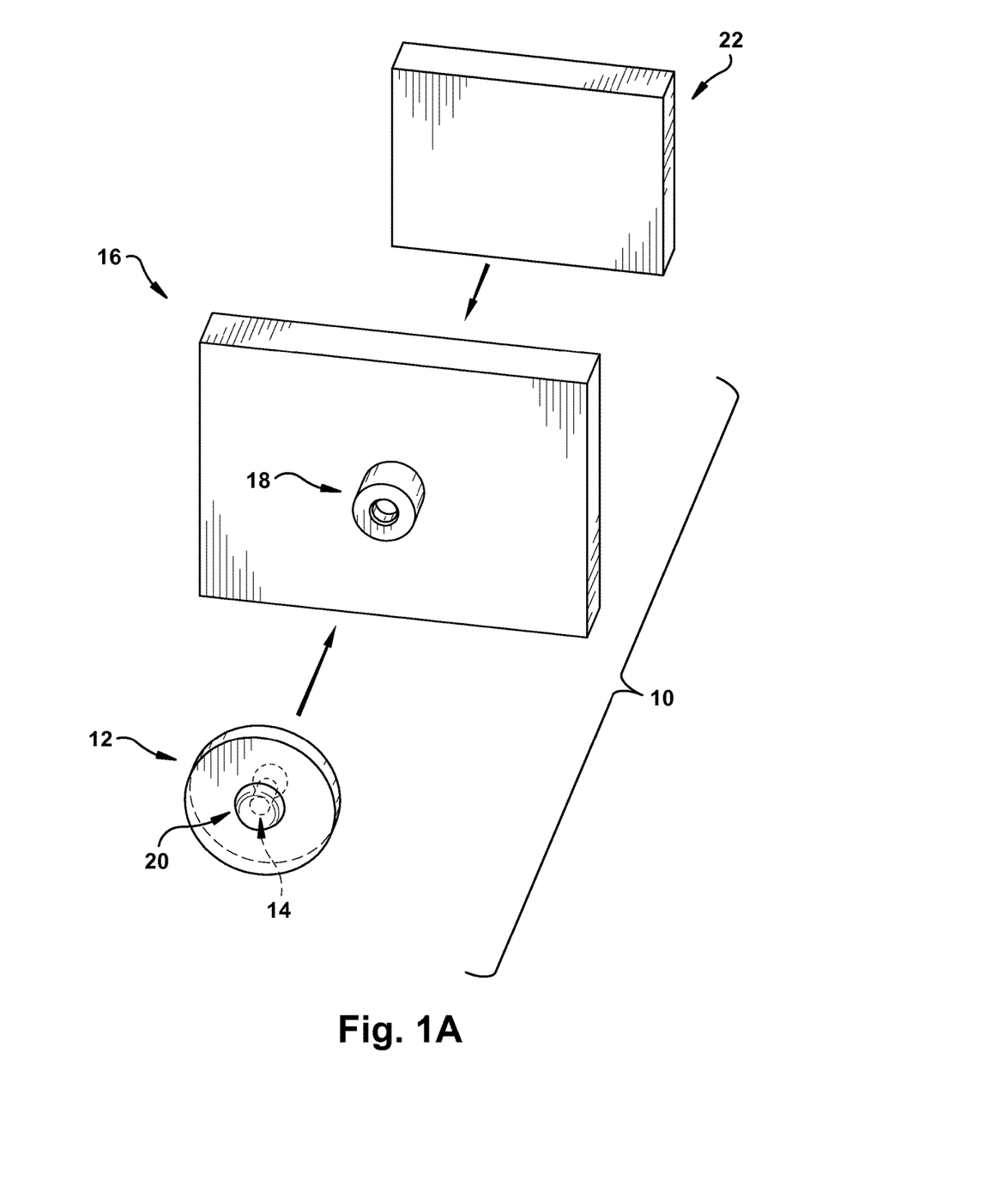
FIG. 1A is an exploded perspective view of a transducer holder assembly constructed in accordance with one aspect of the present disclosure.
Figure 1B:
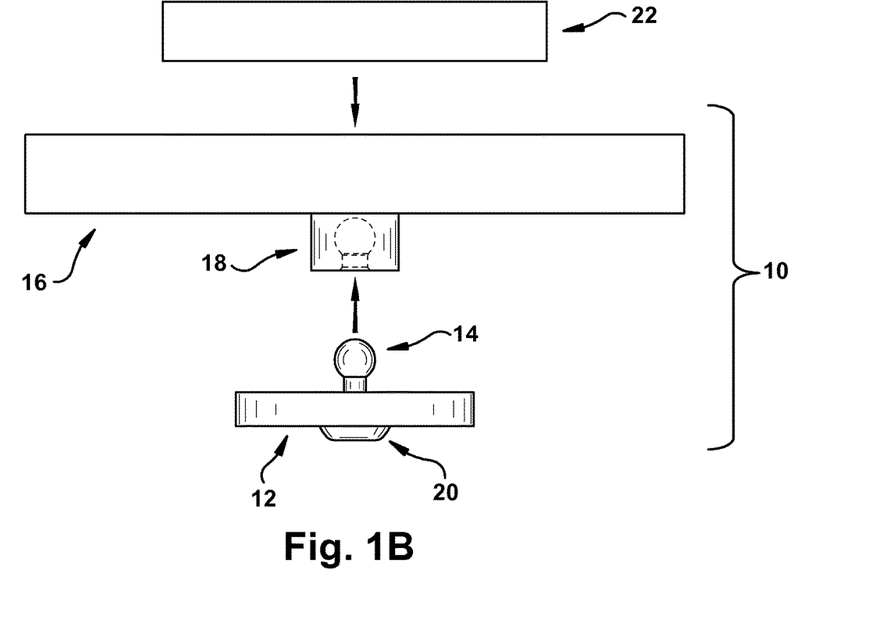
FIG. 1B is a schematic illustration showing a side view of the transducer holder assembly in FIG. 1A.
Figure 1C:
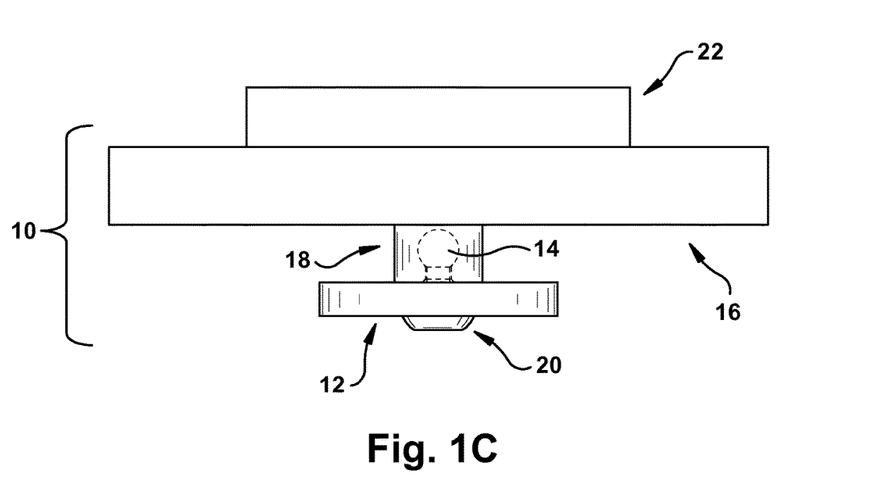
FIG. 1C is a schematic illustration showing the fully-assembled transducer holder assembly in FIGS. 1A-B.

The present disclosure relates generally to a transducer holder and, more particularly, to a mobile transducer holder assembly for use with pressure monitoring and other technologies. As representative of one aspect of the present disclosure, FIGS. 1A-C show a mobile transducer holder assembly 10 configured for direct attachment to a patient. Conventional transducer holders are mounted on medical equipment (e.g., an IV pole) to ensure that a transducer remains in-line with a target organ (e.g., the heart, lungs or brain) of a patient. The vertical location of the transducer holder, however, needs to be adjusted every time the position of the patient is changed to keep a transducer in-line with the target organ. As described in more detail below, the transducer holder assembly 10 of the present disclosure can be directly attached to a patient so that movement of the patient does not require repositioning of a transducer. Advantageously, the transducer holder assembly 10 ensures that a transducer remains properly situated (e.g., in-line) with respect to the target organ, while also reducing the difficulty associated with managing the numerous cords required for operation of the transducer.

One aspect of the present disclosure includes a transducer holder assembly 10 for direct attachment to a patient. The transducer holder assembly 10 can include a support member 12, a first mating member 14 attached to the support member, a housing 16, and a second mating member 18 attached to the housing. The transducer holder assembly 10 can also include an electrode 20 attached to the support member 12. As shown in FIGS. 1A-C, the transducer holder assembly 10 can have a generally rectangular configuration; however, it will be appreciated that the transducer holder assembly can have any suitable shape that allows the transducer holder assembly to securely hold a transducer 22 when directly attached to a patient. For example, the transducer holder assembly 10 can be sized and dimensioned to securely hold any type of transducer 22, including a pulmonary artery pressure transducer, a cerebral intracranial pressure transducer, as well as other technologies. A snap-fit mechanism, which is described in more detail below, advantageously facilitates quick and easy assembly of the transducer holder assembly 10 while also permitting, in some instances, 360-degree rotation of the housing 16 relative to the support member 12. The dimensions of the transducer holder assembly 10 can be varied depending, for example, upon the size of the transducer 22, the patient's anatomy, the particular bodily location for attachment, etc.

Figure 2A:
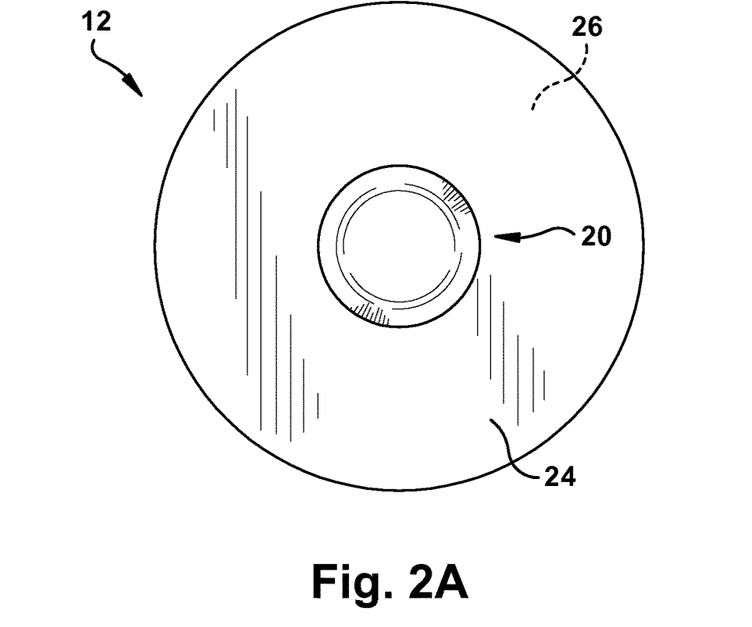
FIG. 2A is a schematic illustration showing a bottom view of a support member and an electrode comprising the transducer holder assembly in FIGS. 1A-C.
Figure 2B:
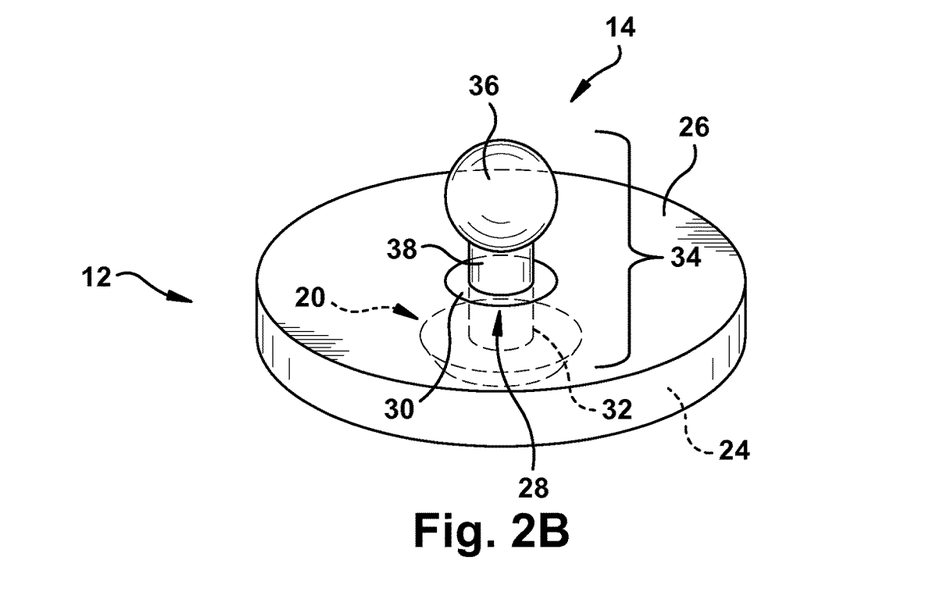
FIG. 2B is a perspective view of a first mating member and the support member in FIG. 2A.

In another aspect, the transducer holder assembly 10 includes a support member 12 (FIGS. 2A-B). The support member 12 can have a disc-shaped configuration; however, other shapes are possible. In one example, the support member 12 can be an electrocardiogram (EKG) pad; however it will be appreciated that the support member can be any suitable, commercially-available pad. The support member 12 can be sized and dimensioned for direct attachment to either a pediatric patient or an adult patient. Regardless of its size, the support member 12 can include a contact surface 24 and an oppositely disposed connection surface 26. The contact surface 24 is configured for direct attachment to the skin of a patient. At least a portion of the contact surface 24 can include an adhesive to facilitate attachment of the support member 12 to the skin of a patient. Although not shown, the support member 12 can further include a peelable layer that overlays the contact surface 24 when the transducer holder assembly 10 is not in use. When attachment of the transducer holder assembly 10 to a patient is desired, the peelable layer can be easily removed to expose the adhesive on the contact surface 24. The support member 12 can be made of a single piece of material or a combination of two or more materials. The support member 12 can have a rigid, semi-rigid, or flexible configuration.

As shown in FIGS. 2A-B, a single electrode 20 is disposed on the contact surface 24; however, it will be appreciated that more than one electrode can be disposed on the contact surface. Although the electrode 20 is shown as being circular in FIGS. 2A-B, it will be appreciated that other shapes are possible. The electrode 20 can be located about any portion of the contact surface 24 (e.g., centrally located).

Figure 4A:
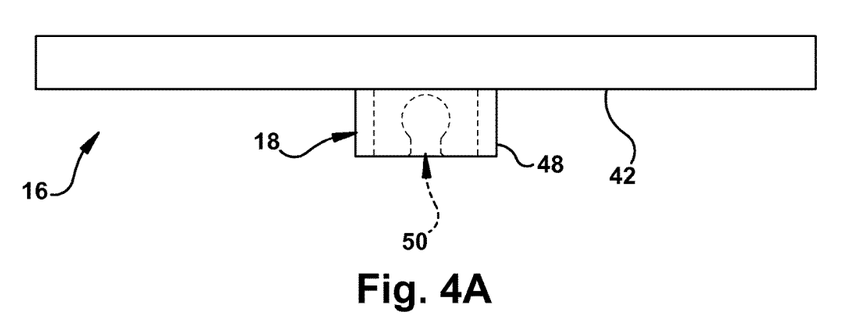
FIG. 4A is a schematic illustration showing a second mating member of the housing in FIG. 3A.

In another aspect, the support member 12 can include a first mating member 14 attached to the connection surface 26. As discussed in more detail below, the first mating member 14 can configured to releasably mate with a second mating member 18 (FIG. 4A), depending on the size of the patient. The first mating member 14 (FIG. 2B) includes a base portion 28 having an upper surface 30, an oppositely disposed lower surface 32, and an attachment portion 34. The attachment portion 34 includes a tip portion 36 and a stem portion 38. The stem portion 38 is integrally formed with the upper surface 30 of the base portion 28. The tip portion 36 has a bulbous configuration adapted to securely mate with the second mating member 18 (FIG. 4A). The first mating member 14 (FIG. 2B) can be axially aligned with, or offset from, the electrode 20 (FIG. 2A). The first mating member 14 (FIG. 2B) can be made of a single piece of material, or alternatively, a combination of two or more pieces of material. The first mating member 14 can have a rigid or semi-rigid configuration.

Figure 3A:
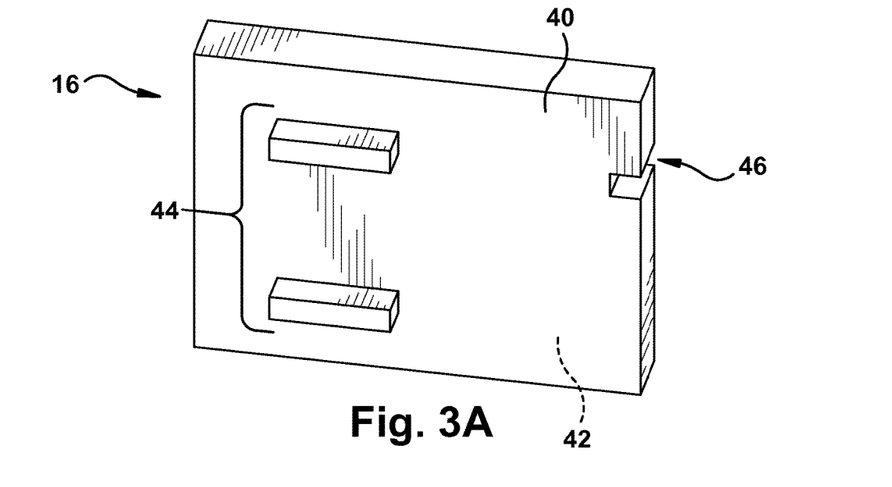
FIG. 3A is a schematic illustration showing a first surface of a housing comprising the transducer holder assembly in FIGS. 1A-C.
Figure 3B:
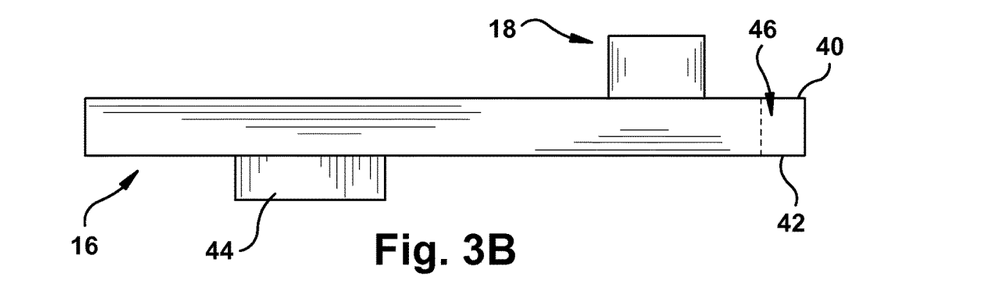
FIG. 3B is a side view of the housing in FIG. 3A.
Figure 3C:
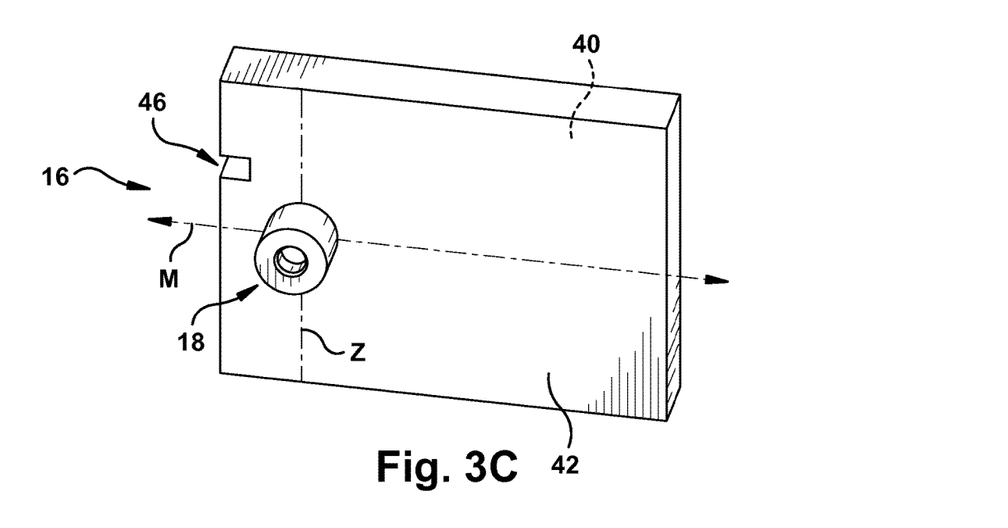
FIG. 3C is a perspective view showing a second surface of the housing in FIG. 3A.

In another aspect, the transducer holder assembly 10 includes a housing 16 (FIGS. 3A-C) configured to receive and hold at least a portion of a transducer 22 (FIGS. 1A-C). The housing 16 (FIGS. 3A-C) can be rectangular; although, other shapes are possible. The housing 16 includes a first surface 40 and an oppositely disposed second surface 42. The first surface 40 includes a locking mechanism 44 configured to secure the transducer 22 (FIGS. 1A-C) to the housing 16 (FIGS. 3A-C). The locking mechanism 44 can include one or more components designed to receive and securely hold the transducer 22 (FIGS. 1A-C) in contact with the housing 16 (FIGS. 3A-C). Examples of such components can include, but are not limited to, clamps, hooks, loops, snaps, ramps, tabs, grooves, adhesives, and the like. The housing 16 can also include a notch 46 configured to hold one or more cords (not shown) associated with the transducer 22 (FIGS. 1A-C). The housing 16 (FIGS. 3A-C) can be made of a single piece of material or, alternatively, two or more pieces of material. For example, the housing 16 can be made of a metal (e.g., aluminum, steel, etc.) or a non-metal material (e.g., rubber, plastic, etc.). The housing 16 can have a rigid, semi-rigid, or flexible configuration. In one example, the housing 16 can be configured in a similar or identical manner as a device commercially available from ICU Medical Aust Pty. Ltd (e.g., Mount List No. 011-42582-01, 011-42582-02 or 011-42582-06) (New South Wales, Australia). It will be appreciated that the housing 16 can be altered in any suitable manner to create a generally flat surface (e.g., removing extraneous portions of the housing, filling gaps in the housing, etc.). In another example, the housing 16 can include a zero-line Z (FIG. 3C) that extends perpendicular to a longitudinal midline M. The zero-line Z can be disposed on a portion of the second surface 42 of the housing 16. The zero-line Z and the midline M can be used as guides to position a second mating member 18 on the second surface 42 of the housing 16, as described below.

Figure 4B:
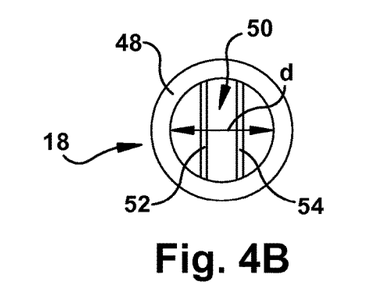
FIG. 4B is a top view of the second mating member in FIG. 4A.
Figure 4C:
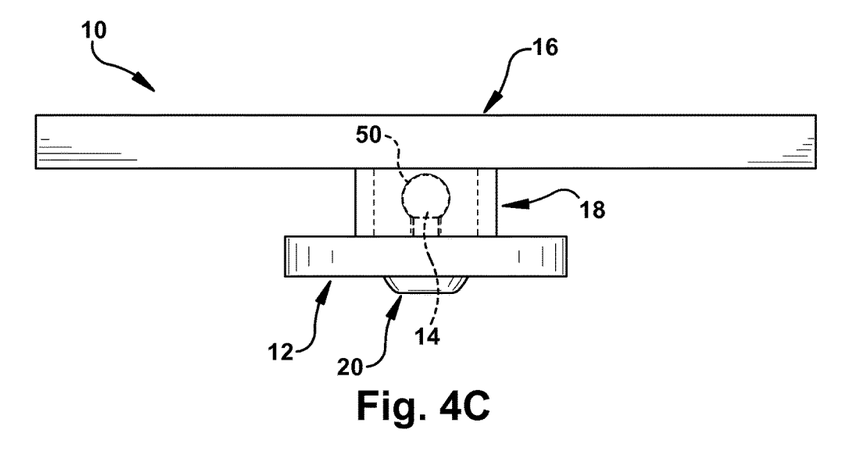
FIG. 4C is a schematic illustration showing the second mating member engaging the first mating member in FIG. 2B.

In another aspect, the housing 16 includes a second mating member 18 (FIGS. 4A-C) coupled thereto. The second mating member 18 is configured to releasably mate with the first mating member 14 (FIG. 2B) via a snap-fit mechanism. The second mating member 18 (FIGS. 4A-C) includes a main body 48 and a channel 50 centrally located therein. In one example, the channel 50 includes a diameter d that is sized and dimensioned to receive the tip portion 36 of the first mating member 14 (FIG. 2B). The main body 48 (FIG. 4B) includes first and second tension rods 52 and 54 located within a portion of the channel 50. The tension rods 52 and 54 are radially displaced upon insertion of the tip portion 36 of the first mating member 14 (FIG. 2B) into the channel 50 (FIG. 4C) to secure the first mating member to the second mating member 18. The tension rods 52 and 54 can return to their original configuration once the tip portion 36 is fully inserted into the channel 50. The second mating member 18 can be made of a single piece of material or, alternatively, a combination of two or more pieces of material. Examples of such materials can include metals (e.g., aluminum, steel, etc.) and non-metals (e.g., rubbers, plastics, etc.). In some instances, the second mating member 18 can be located on the second surface 42 of the housing 16 at the intersection of the midline M and the zero-line Z. In other instances, the second mating member 18 can be located on any other suitable location on the second surface 42 of the housing 16 (e.g., centrally located). The second mating member 18 can be attached to the second surface 42 of the housing 16 in any suitable manner (e.g., gluing, welding, etc.). Alternatively, the second mating member 18 can be integrally formed with the second surface 42 of the housing 16.

Figure 5A:
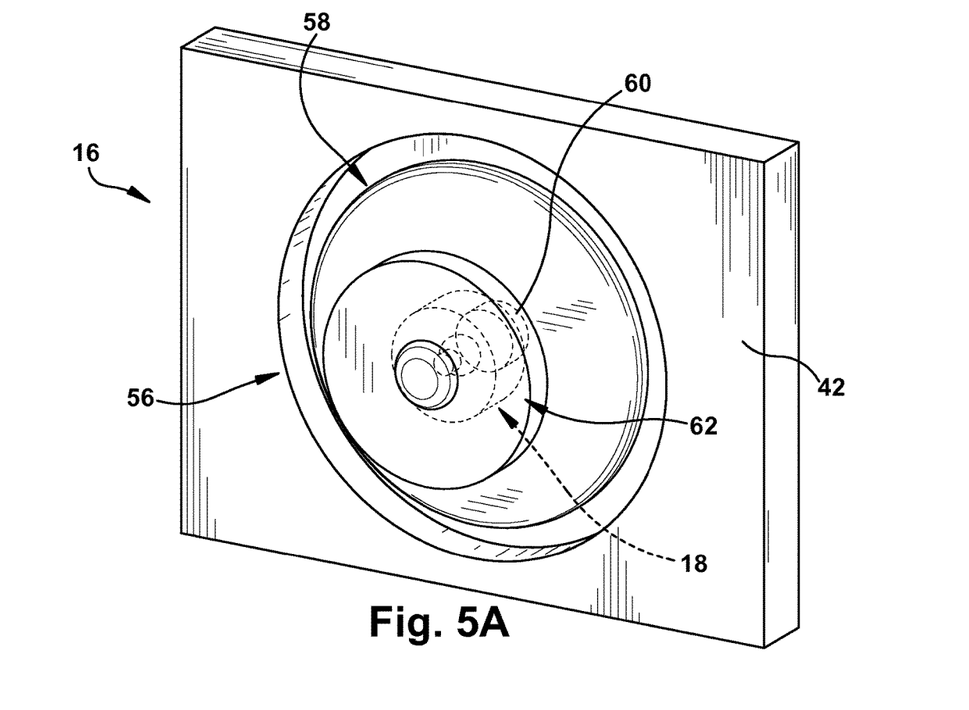
FIG. 5A is a perspective view of a second surface of a transducer holder assembly constructed in accordance with another aspect of the present disclosure.
Figure 5B:
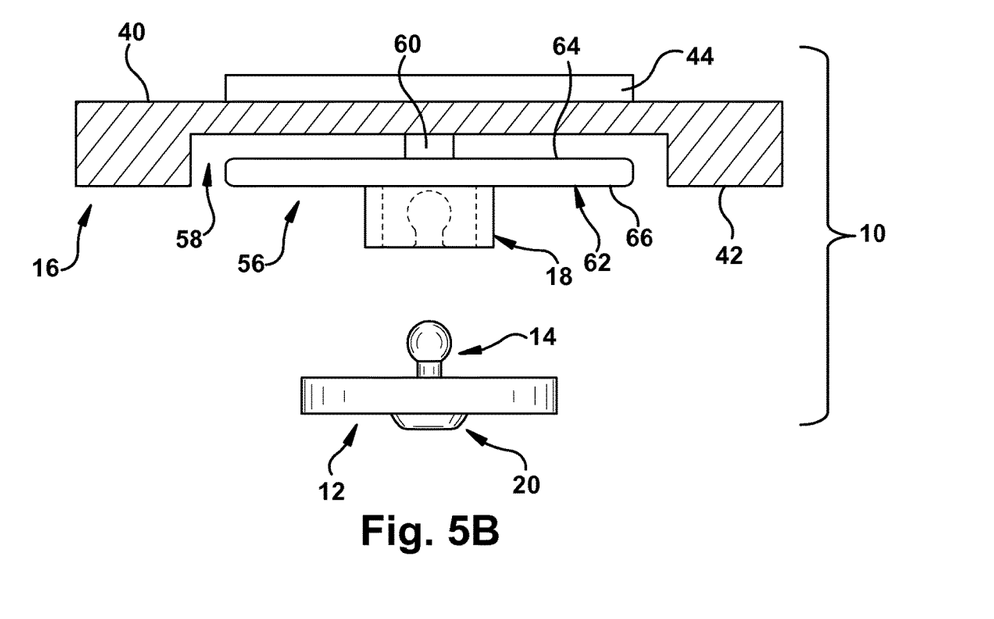
FIG. 5B is a perspective view the transducer holder assembly in FIG. 5A engaging the support member of FIGS. 2A-B.

FIGS. 5A-B illustrate an alternative construction of the transducer holder assembly 10 in which the housing 16 includes a joint mechanism 56. The joint mechanism 56 is configured to permit rotation of the housing 16 up to (and including) 360-degrees relative to the support member 12 when the first mating member 14 is mated with the second mating member 18. The joint mechanism 56 includes a recessed portion 58 of the housing 16, a swivel 60, a rotatable main body 62, and the second mating member 18. The recessed portion 58 includes a depression or alcove configured to accommodate the rotatable main body 62. The swivel 60 is sandwiched between the recessed portion 58 and the rotatable main body 62. The swivel 60 permits rotation of the rotatable main body 62 relative to the housing 16. The rotatable main body 62 has a disc-like configuration and is rotatable 360-degrees about the swivel 60. In some instances, the rotatable main body 62 is disposed within the recessed portion 58 such that a lower surface 64 of the rotatable main body is flush with the second surface 42 of the housing 16. The second mating member 18, as described above, is attached to an upper surface 66 of the rotatable main body 62.

Figure 6:
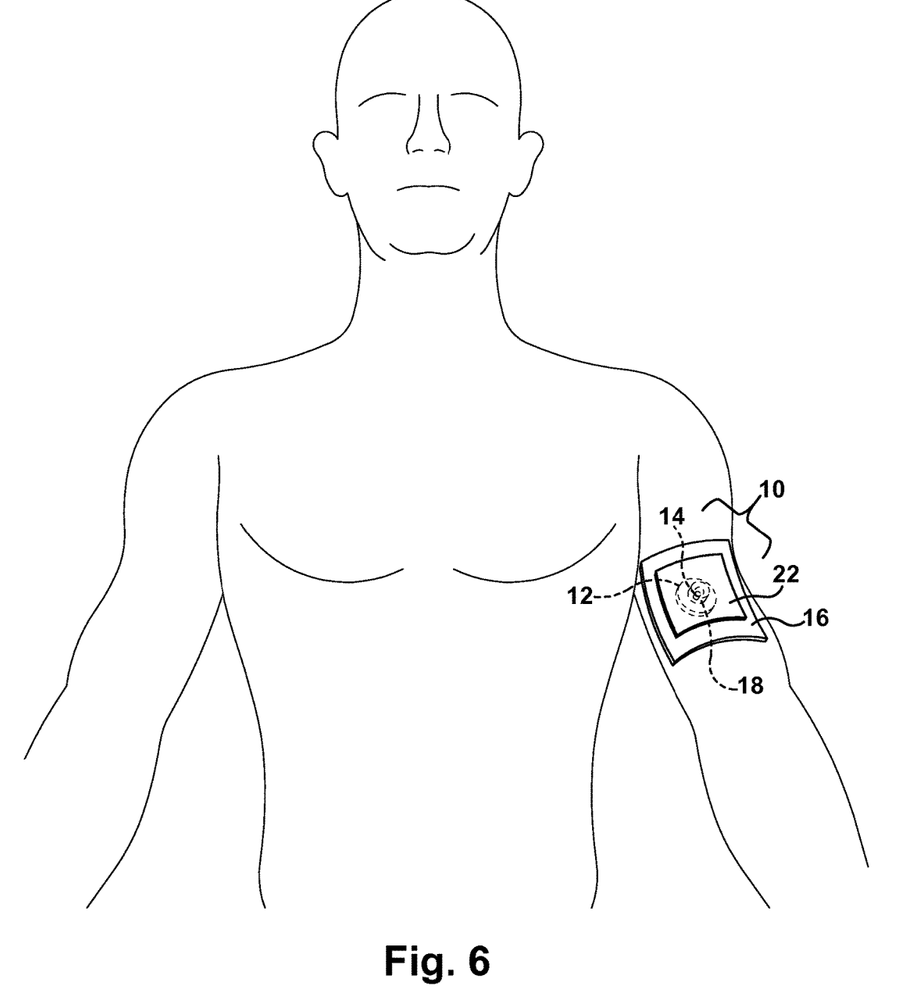
FIG. 6 is a schematic illustration showing the transducer holder assembly in FIGS. 1A-C attached to an arm of a patient.

One example use of the transducer holder assembly 10 is illustrated in FIG. 6. Before attachment to a patient, the support member 12 and the housing 16 are joined together to form the transducer holder assembly 10. The type of support member 12 is selected based on the size of the patient (e.g., pediatric-sized or adult-sized). In one example, the support member 12 and the housing 16 are joined together by engaging the first mating member 14 with the second mating member 18 via a snap-fit mechanism (described above). The snap-fit mechanism permits the housing 16 to rotate 360-degrees relative to the support member 12 when the first and second mating members 14 and 18 are mated with one another. Once the support member 12 and the housing 16 are connected with one another, the transducer 22 is secured to the housing 16 via the locking mechanism 44.

Now assembled, the transducer holder assembly 10 is directly attached to the patient. By "directly attached," it is meant that the transducer holder assembly 10, and in particular the support member 12, is secured to a portion of the skin of the patient so that the contact surface 24 is in physical contact with the skin without any intervening structures, elements, or materials therebetween. In some instances, an adhesive can be applied to a portion of the contact surface 24 of the support member 12 before attachment of the transducer holder assembly 10 to the patient. Alternatively, the peelable layer can be removed from the support member 12 to expose the adhesive. The support member 12 can then be applied to the patient so that the contact surface 24 directly contacts the patient's skin. When the transducer holder assembly 10 is attached to the patient (e.g., the patient's arm), the transducer holder assembly is free from attachment to any medical equipment associated with the patient. Additionally, the transducer 22 can remain perpendicular, or substantially perpendicular, to the ground during movement of the patient, which ensures that the transducer remains in-line with a target organ of the patient (e.g., the heart).

Figure 7A:
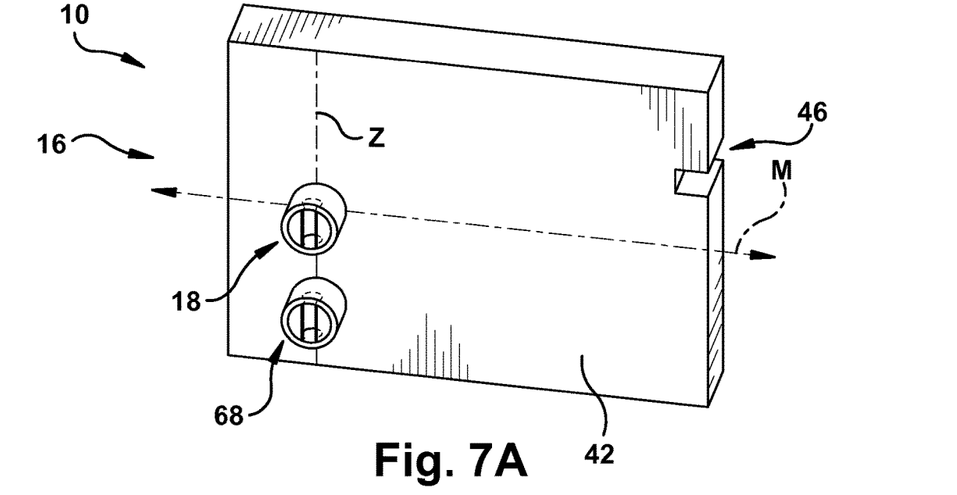
FIG. 7A is a perspective view showing an alternative configuration of the transducer holder assembly in FIGS. 1A-C.
Figure 7B:
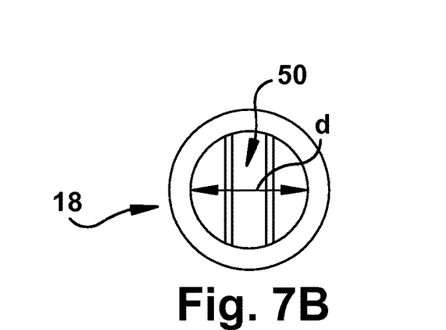
FIG. 7B is a top view showing the second mating member of FIG. 7A.
Figure 7C:
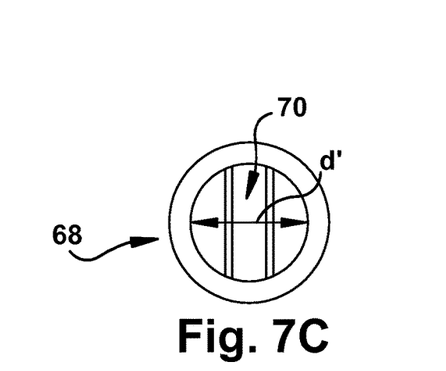
FIG. 7C is a top view showing the third mating member of FIG. 7A.

FIGS. 7A-C illustrate an alternative configuration of the transducer holder assembly 10 in which the housing 16 includes a third mating member 68. The third mating member 68 can have a size and shape that is the same as, or different than, the size and shape of the second mating member 18. Regardless of its dimensions, a channel 70 (FIG. 7C) of the third mating member 68 can include a diameter d' that is different than the diameter d of the channel 50 (FIG. 7B) of the second mating member 18. For example, the channel 50 of the second mating member 18 can be configured to releasably mate with a pediatric-sized support member 12, while the channel 70 of the third mating member 68 can be configured to releasably mate with an adult-sized support member (or vice-versa). In some instances, the third mating member 68 can be located on the second surface 42 of the housing 16 adjacent the second mating member 18. It will be appreciated that the third mating member 68 can be located at a variety of locations on the second surface 42 of the housing 16 (e.g., centrally located). It will also be appreciated that the third mating member 68 can be associated with the joint mechanism 56 (FIGS. 5A-B) or, alternatively, that the second mating member 18 and the third mating member can each be associated with separate joint mechanisms. Advantageously, the addition of the third mating member 68 (FIGS. 7A-C) to the housing 16 provides a user with the ability to use the transducer holder assembly with a pediatric or an adult-sized patient regardless of the size of the support member 12.

Figure 8A:
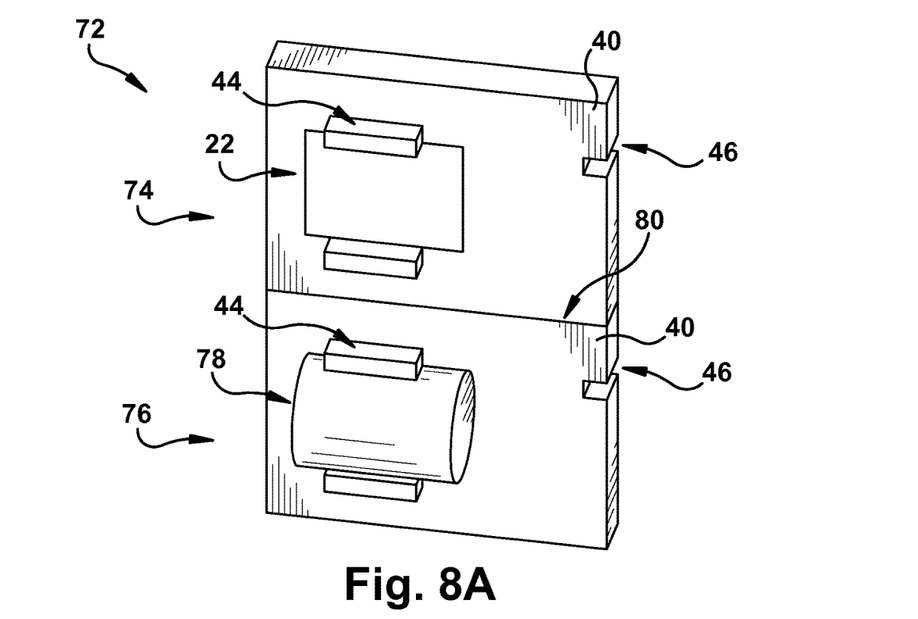
FIG. 8A is a perspective view showing a first surface of each of a first and second housing comprising another alternative configuration of the transducer holder assembly in FIGS. 1A-C.
Figure 8B:
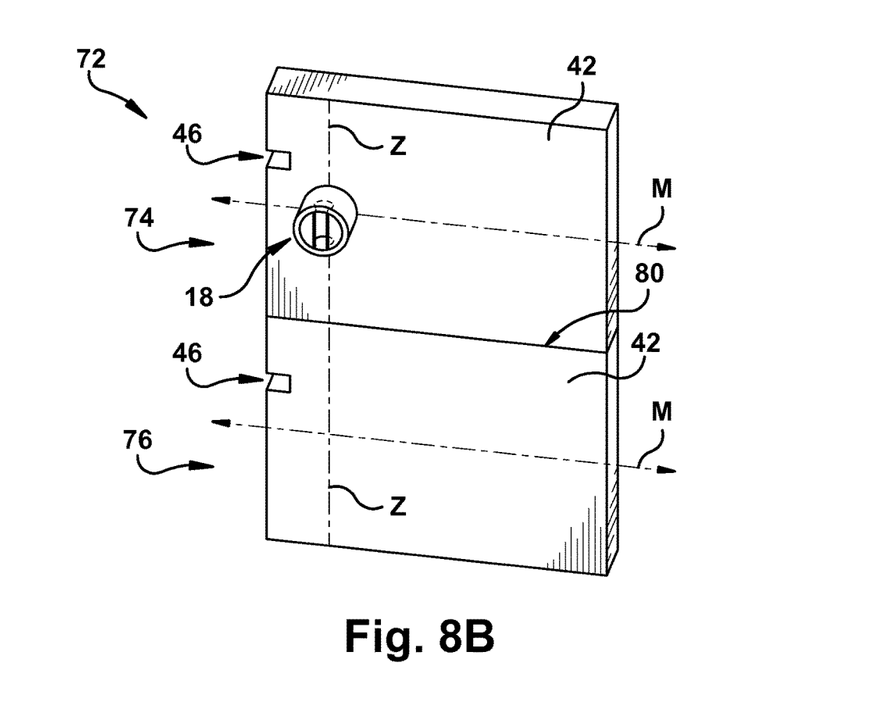
FIG. 8B is a perspective view showing a second surface of each of the first and second housings of the transducer holder assembly in FIG. 8A.

An alternative configuration of the transducer holder assembly 10 is shown in FIGS. 8A-B. A transducer holder assembly 72 of FIGS. 8A-B can be identically constructed as the transducer holder assembly 10 of FIGS. 1A-C, except as described below. In this configuration, the transducer holder assembly 72 (FIGS. 8A-B) can include a first housing 74 and a second housing 76. The first housing 74 can be configured to securely hold the transducer 22, and the second housing 76 can be configured to securely hold a line-clearing mechanism 78 (e.g., a plunger capable of clearing IV tubing) that is associated with the transducer (or vice-versa). The first and second housings 74 and 76 can be attached along a common leading edge 80 such that the transducer 22 and the line-clearing mechanism 78 are arranged substantially parallel to each other. The first and second housings 74 and 76 can have a size and shape that is the same as, or different than, the size and shape of the housing 16 shown in FIGS. 3A-C. Regardless of their dimensions, the first and second housings 74 and 76 (FIGS. 8A-B) can each include substantially the same features as the housing 16 (FIGS. 3A-B) (e.g., first and second surfaces 40 and 42, a locking mechanism 44, a notch 46, a midline M, a zero-line Z, etc.). For example, the first surface 40 of the first housing 74 (FIG. 8A) can include a locking mechanism 44 to securely hold the transducer 22. The first surface 40 of the second housing 76 can also include a locking mechanism 44 for securely holding the line-clearing mechanism 78. It will be appreciated that the second mating member 18 can be attached to whichever of the first or second housing 74 or 76 that holds the transducer 22. For example, the second surface 42 of the first housing 74 can include the second mating member 18 (FIG. 8B) attached thereto (as described above). In another example, the second surface 42 of the first housing 74 can include the third mating member 68 attached thereto (as described above). Although not shown, the first housing 74 can include one or more joint mechanisms 56 (described above) that is/are associated with the second mating member 18 and/or the third mating member 68. Advantageously, the addition of the second housing 76 provides a user with the ability to use the transducer holder assembly with additional medical devices (besides a transducer) when treating a patient.

From the above description of the present disclosure, those skilled in the art will perceive improvements, changes and modifications. For example, it will be appreciated that the transducer holder assembly 10 or the transducer holder assembly 72 can be attached to a piece of clothing or medical equipment associated with the patient. Such improvements, changes, and/or modifications are within the skill of the art and are intended to be cover by the appended claims.

What is claimed is:

1. A transducer holder assembly for attachment to a patient, the transducer holder assembly comprising:
   a support member having a contact surface and an oppositely disposed connection surface;
   at least one electrode disposed on the contact surface;
   a first mating member coupled to the connection surface; and
   a housing configured to receive and hold at least a portion of a transducer, the housing including a second mating member configured to releasably mate with the first mating member via a snap-fit mechanism, wherein the snap-fit mechanism permits the housing to rotate 360-degrees relative to the contact surface and the oppositely disposed connection surface when the first mating member and the at least one second mating member are mated with one another.

2. The transducer holder assembly of claim 1, being configured such that the transducer remains substantially perpendicular to the ground during movement of the patient.

3. The transducer holder assembly of claim 1, being free from attachment to a piece of medical equipment associated with the patient when the transducer holder assembly is attached to the patient.

4. The transducer holder assembly of claim 1, being configured for direct attachment to the skin of the patient.

5. The transducer holder assembly of claim 1, wherein at least a portion of the contact surface includes an adhesive disposed thereon.

6. The transducer holder assembly of claim 1, wherein the housing additionally includes a joint mechanism configured to permit the rotation of the housing 360-degrees relative to the support member when the first mating member and the at least one second mating member are mated with one another.

7. The transducer holder assembly of claim 1, wherein the housing further includes a third mating member, one of the second and third mating members is configured for use with a pediatric-sized patient and the other of the second and third mating members is configured for use with an adult-sized patient.

8. A transducer holder assembly for attachment to a patient, the transducer holder assembly comprising:
   a support member having a contact surface and an oppositely disposed connection surface;
   at least one electrode disposed on the contact surface;

a first mating member coupled to the connection surface;
a first housing configured to receive and hold at least a portion of a transducer; and
a second housing connected to a portion of the first housing, the second housing being configured to receive and hold at least a portion of a line-clearing mechanism;
wherein at least one of the first housing and the second housing includes a second mating member configured to releasably mate with the first mating member via a snap-fit mechanism.

9. The transducer holder assembly of claim 8, being configured such that the transducer remains substantially perpendicular to the ground during movement of the patient.

10. The transducer holder assembly of claim 8, being free from attachment to a piece of medical equipment associated with the patient when the transducer holder assembly is attached to the patient.

11. The transducer holder assembly of claim 8, being configured for direct attachment to the skin of the patient.

12. The transducer holder assembly of claim 8, wherein at least a portion of the contact surface includes an adhesive disposed thereon.

13. The transducer holder assembly of claim 8, wherein the snap-fit mechanism permits the housing to rotate 360-degrees relative to the support member when the first mating member and the at least one second mating member are mated with one another.

14. The transducer holder assembly of claim 8, wherein the housing additionally includes a joint mechanism configured to permit rotation of the housing 360-degrees relative to the support member when the first mating member and the at least one second mating member are mated with one another.

15. The transducer holder assembly of claim 8, wherein the housing further includes a third mating member, one of the second and third mating members is configured for use with a pediatric-sized patient and the other of the second and third mating members is configured for use with an adult-sized patient.

16. A method comprising:
providing a transducer holder assembly, the pressure transducer assembly including a support member, at least one electrode, a first mating member and a housing, the support member having a contact surface and an oppositely disposed connection surface, the at least one electrode being disposed on the contact surface, the first mating member being coupled to the connection surface, and the housing being configured to receive and hold at least a portion of the transducer, the housing including a second mating member configured to releasably mate with the first mating member via a snap-fit mechanism, wherein the snap-fit mechanism permits the housing to rotate 360-degrees relative to the contact surface and the oppositely disposed connection surface when the first mating member and the at least one second mating member are mated with one another;
directly attaching the transducer holder assembly to a portion of the skin of a patient; and
attaching a transducer to the housing via the snap-fit mechanism.

17. The method of claim 16, wherein the transducer holder assembly is attached to the patient so that the transducer holder assembly is free from attachment to any medical equipment associated with the patient.

18. The method of claim 16, wherein the transducer holder assembly remains substantially perpendicular to the ground during movement of the patient such that the transducer remains in-line with a target organ of the patient.

19. The method of claim 16, wherein the housing is free to rotate the 360-degrees relative to the support member during movement of the patient.

* * * * *